United States Patent
Chou et al.

(10) Patent No.: US 11,684,742 B2
(45) Date of Patent: *Jun. 27, 2023

(54) NASAL CANNULA DEVICE

(71) Applicant: FOXXMED LTD., Yilan County (TW)

(72) Inventors: Jeng-Yu Chou, Yilan County (TW); Kuang-Ming Chiang, Yilan County (TW)

(73) Assignee: FOXXMED LTD., Yilan County (TW)

( * ) Notice: Subject to any disclaimer, the term of this patent is extended or adjusted under 35 U.S.C. 154(b) by 308 days.

This patent is subject to a terminal disclaimer.

(21) Appl. No.: 17/115,150

(22) Filed: Dec. 8, 2020

(65) Prior Publication Data

US 2021/0085906 A1 Mar. 25, 2021

Related U.S. Application Data (63) Continuation of application No. 16/038,124, filed on Jul. 17, 2018, now Pat. No. 10,905,840.

(51) Int. Cl.
*A61M 16/06* (2006.01)
*A61M 16/08* (2006.01)
*A61M 16/16* (2006.01)

(52) U.S. Cl.
CPC .... *A61M 16/0666* (2013.01); *A61M 16/0672* (2014.02); *A61M 16/0816* (2013.01); *A61M 16/16* (2013.01); *A61M 2202/0208* (2013.01); *A61M 2205/0216* (2013.01); *A61M 2205/42* (2013.01)

(58) Field of Classification Search
CPC .............. A61M 16/06; A61M 16/0666; A61M 16/0672
See application file for complete search history.

(56) References Cited

U.S. PATENT DOCUMENTS

| 10,905,840 | B2* | 2/2021 | Chou | A61M 16/0666 |
|---|---|---|---|---|
| 2005/0028822 | A1* | 2/2005 | Sleeper | A61M 16/0833 |
| | | | | 128/207.18 |
| 2006/0237017 | A1* | 10/2006 | Davidson | A61M 16/0622 |
| | | | | 128/205.25 |
| 2007/0272249 | A1* | 11/2007 | Chandran | A61M 16/20 |
| | | | | 128/206.28 |
| 2016/0015921 | A1* | 1/2016 | Harrison | A61M 16/0666 |
| | | | | 128/205.25 |
| 2019/0060599 | A1* | 2/2019 | Johnson | A61M 16/0087 |

FOREIGN PATENT DOCUMENTS

GB 2493520 A * 2/2013 ........ A61M 16/0666

* cited by examiner

*Primary Examiner* — Joseph D. Boecker
(74) *Attorney, Agent, or Firm* — NZ Carr Law Office (57) ABSTRACT

A nasal cannula device includes a cannula body. The cannula body includes an accommodating chamber inside and includes two nasal joint tube extended outwardly and communicating with the accommodating chamber. A junction ring is formed between the cannula body and each nasal joint tube. At least one of the cannula body and each nasal joint tube includes a recessed annular section recessed at one side of each junction ring. The recessed annular section has a thickness smaller than a thickness of the cannula body, a thickness of each nasal joint tube, and a thickness of each junction ring. Accordingly, the nasal cannula device can deliver a therapeutic gas smoothly.

1 Claim, 11 Drawing Sheets

NASAL CANNULA DEVICE

CROSS-REFERENCE TO RELATED APPLICATION

This application is a continuation application of U.S. application Ser. No. 16/038,124 filed Jul. 17, 2018, which is incorporated herein by reference in its entirety.

BACKGROUND OF THE INVENTION

1. Field of the Invention

The present invention relates to a medical respiratory treatment device and, in particular, to a nasal cannula device.

2. Description of Related Art

A nasal cannula device is one of medical respiratory treatment devices, and is inserted in the nostrils of a patient and used to deliver supplemental oxygen or a humidified therapeutic gas to the patient's respiratory tract.

A conventional nasal cannula device includes a cannula body and two nasal joint tube and a wearing member assembled to the cannula body. The cannula body is connected to a gas delivery tube, the nasal joint tubes are inserted in a patient's two nostrils, the wearing member is put on the patient's head, and a therapeutic gas is delivered into a nasal cavity of the patient through in sequence the gas delivery tube, the cannula body and the nasal joint tube.

However, the nasal cannula device has the following disadvantages. The nasal joint tube has a narrow bore and a thin tube wall, so the nasal joint tube easily bends and deforms when it is under stress. The farther a bent portion of the nasal joint tube is from the body, the more the bent portion can deform, which could cause closing of the nasal joint tube and jeopardize the patient's health. Therefore, the industries aim to provide a nasal cannula device which can prevent the nasal joint tube from being closed by stress on the nasal joint tube.

In view of this, the inventor studied various technologies and created an effective solution in the present disclosure.

SUMMARY

The present invention provides a nasal cannula device. When a nasal joint tube is under stress, the stress is mainly directed to the recessed annular section to thereby prevent deformation of other portions of the nasal joint tube. By this way, the nasal cannula device can deliver a gas smoothly.

The present invention provides a nasal cannula device. The nasal cannula device includes a cannula body. The cannula body includes an accommodating chamber inside and includes two nasal joint tubes extended outwardly and communicating with the accommodating chamber. A junction ring is formed between the cannula body and each of the nasal joint tubes. At least one of the cannula body and each nasal joint tube includes a recessed annular section recessed at one side of each of the junction rings. The recessed annular section has a thickness smaller than a thickness of the cannula body, a thickness of each nasal joint tube and a thickness of each junction ring.

Accordingly, when the nasal joint tube is under stress, the stress is mainly directed to the recessed annular section since it has the thinnest thickness, so other portions of the nasal joint tube is prevented from deformation, and only the recessed annular section deforms. Connected to the junction ring, a portion of the recessed annular section close to the junction ring thus has sufficient strength to resist deformation and is prevented from being overly bent to cause closing of the nasal joint tube. As a result, the recessed annular section does not overly bend to close the nasal joint tube, and therefore the nasal cannula device can deliver the therapeutic gas smoothly.

BRIEF DESCRIPTION OF THE DRAWINGS

The disclosure will become more fully understood from the detailed description and the drawings given herein below for illustration only, and thus does not limit the disclosure, wherein.

DETAILED DESCRIPTION

Detailed descriptions and technical contents of the present disclosure are illustrated below in conjunction with the accompanying drawings. However, it is to be understood that the descriptions and the accompanying drawings disclosed herein are merely illustrative and exemplary and not intended to limit the scope of the present disclosure.

Please refer to FIGS. 1 to 7 for a nasal cannula device according to the first embodiment of the present invention. The nasal cannula device 10 includes a cannula body 1.

Referring to FIGS. 1 to 7, the cannula body 1 includes an accommodating chamber 11 inside and includes two nasal joint tubes 12. The two nasal joint tubes 12 are extended outwardly and communicate with the accommodating chamber 11. A junction ring 13 is formed between the cannula body 1 and each nasal joint tube 12. At least one of the cannula body 1 and each nasal joint tube 12 include a recessed annular section 14a recessed at one side of each junction ring 13.

The recessed annular section 14a has a thickness d smaller than a thickness a of the cannula body 1, a thickness b of each nasal joint tube 12 and a thickness c of each junction ring 13.

Figure 1:
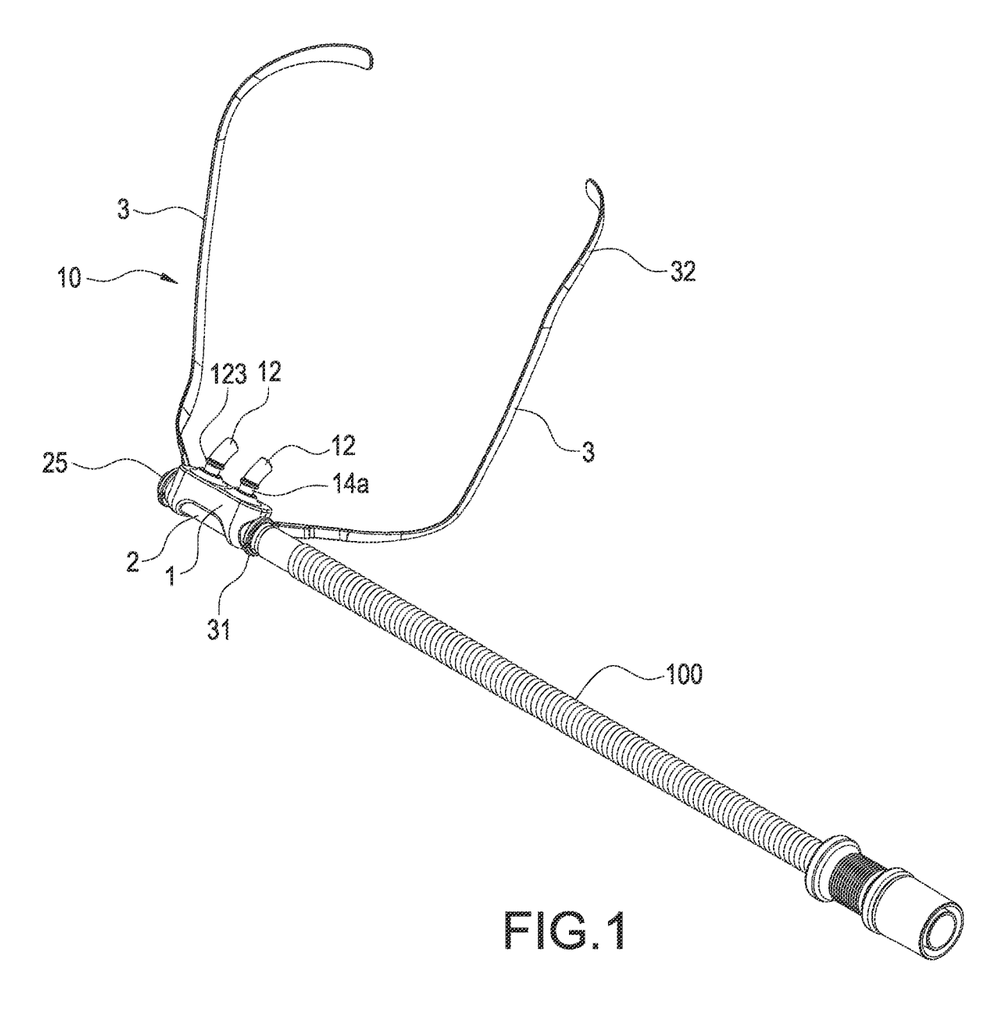
FIG. 1 is a perspective view illustrating a nasal cannula device according to one embodiment of the present invention.
Figure 2:
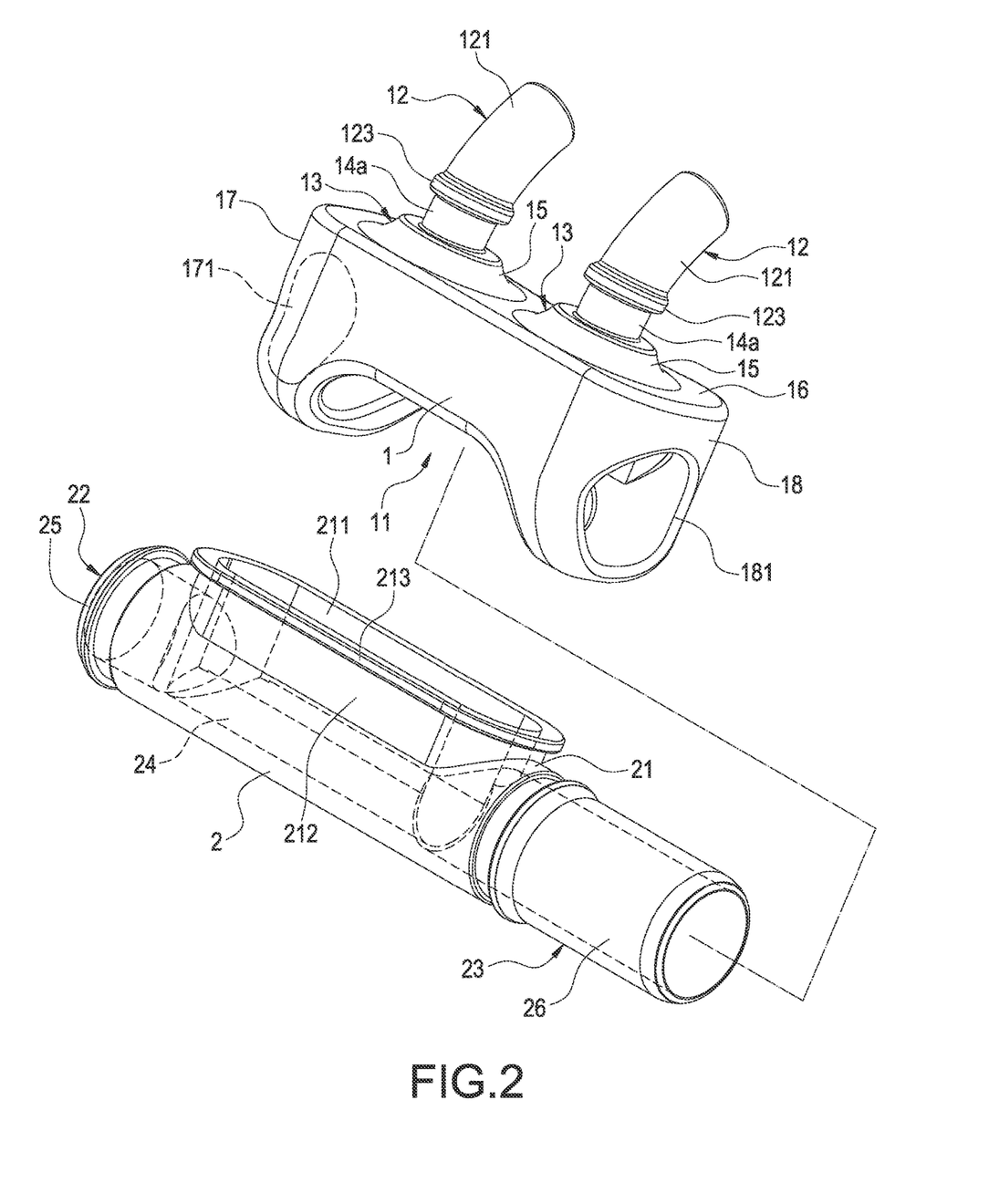
FIG. 2 is a perspective exploded view illustrating a cannula body and a hollow base of the nasal cannula device of FIG. 1.
Figure 3:
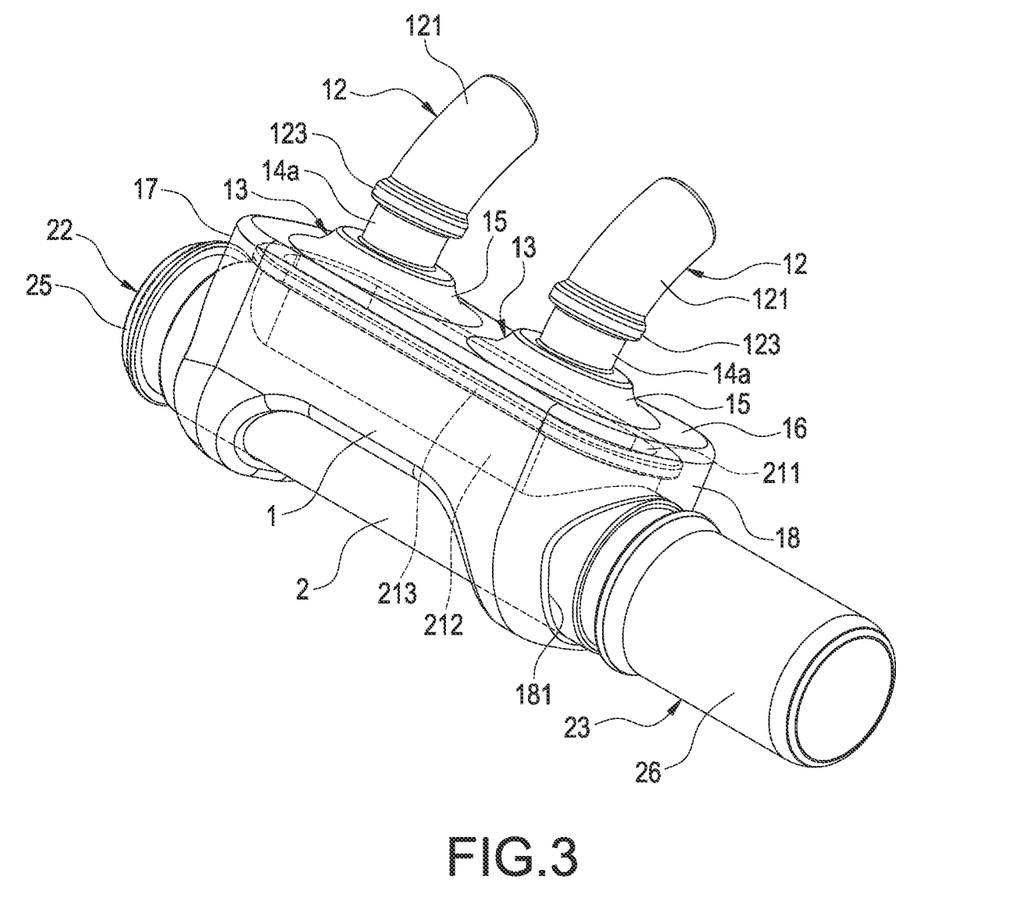
FIG. 3 is a perspective assembled view illustrating the cannula body and the hollow base of the nasal cannula device of FIG. 1.
Figure 4:
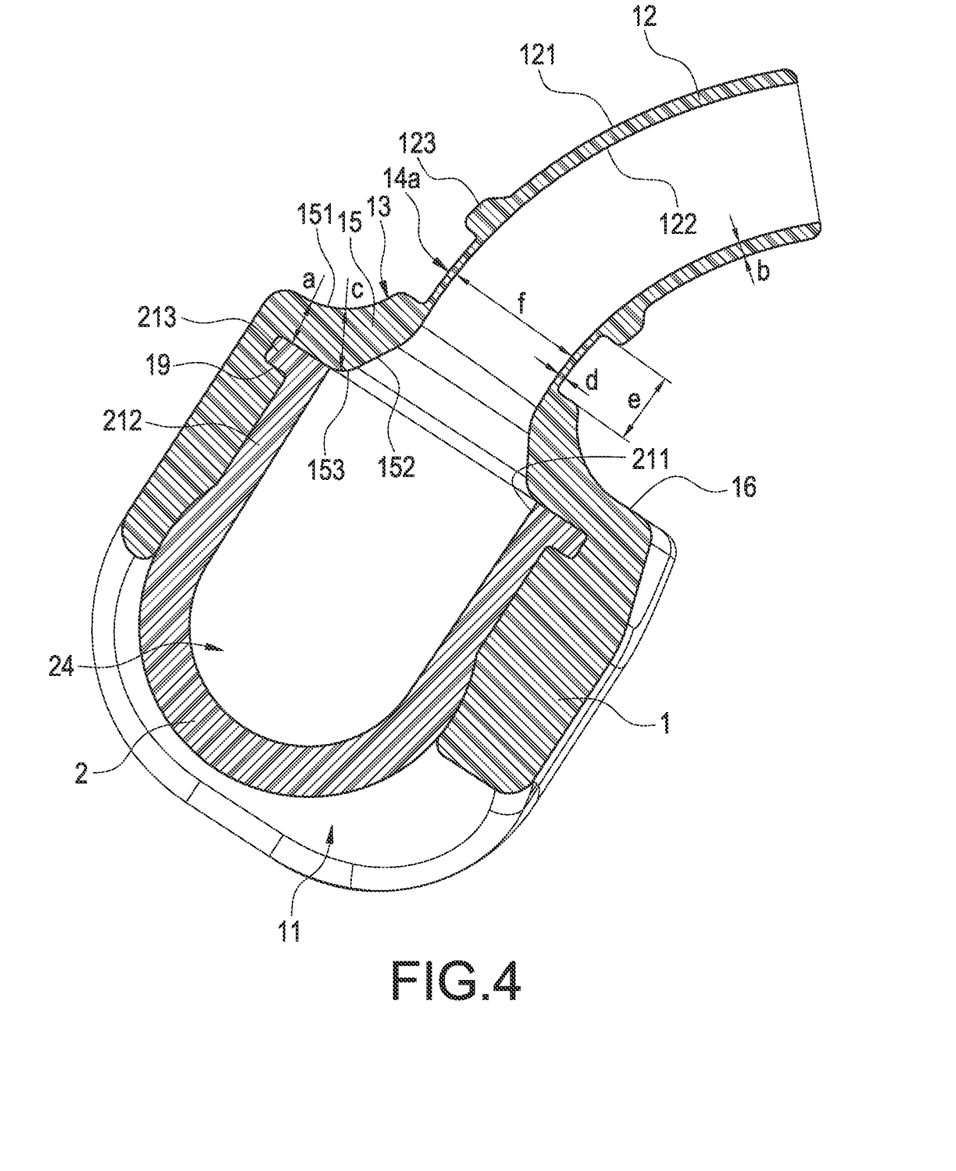
FIG. 4 is a partial cross-sectional view of the nasal cannula device according to the first embodiment of the present invention.
Figure 5:
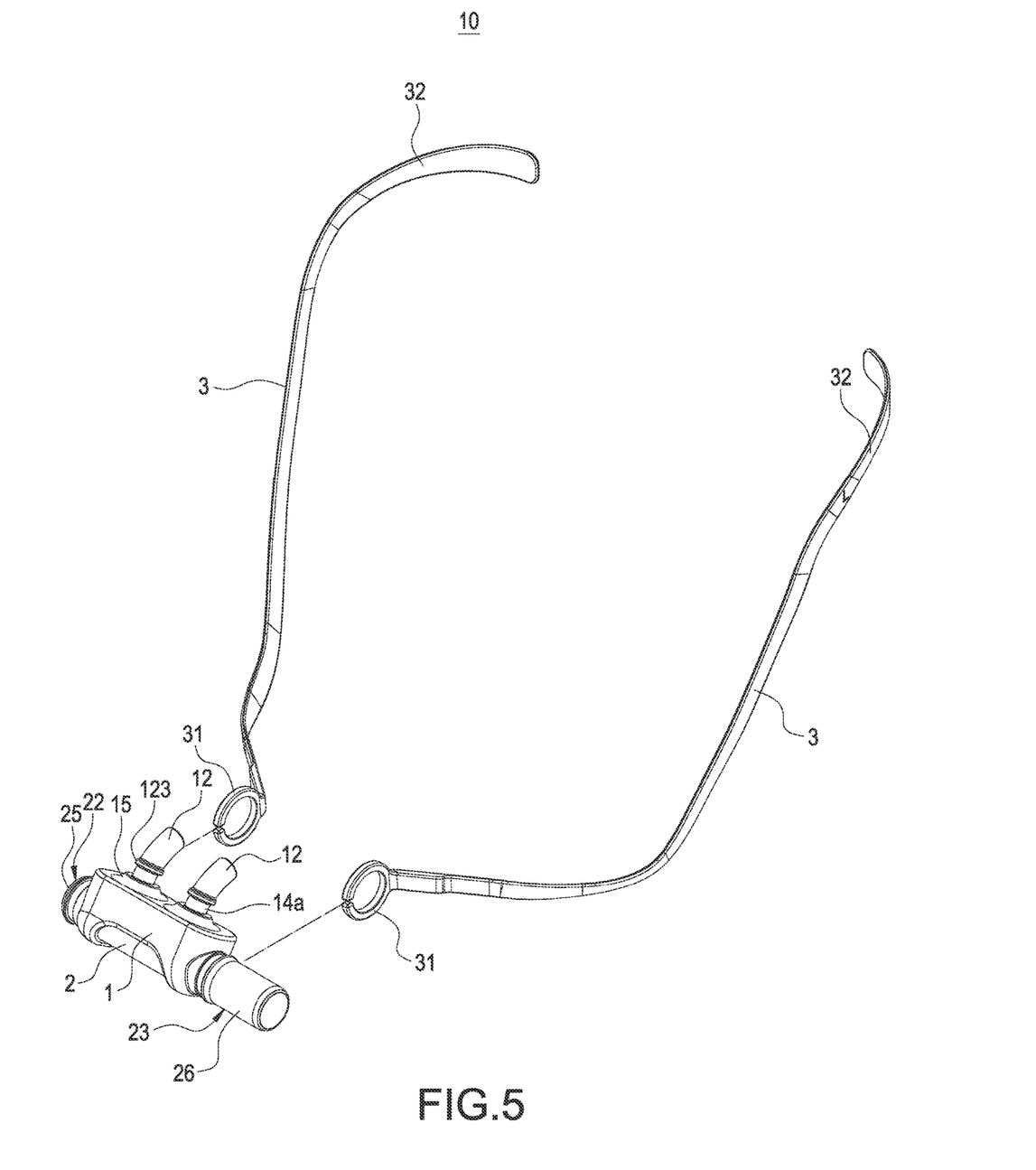
FIG. 5 is a perspective exploded view illustrating the hollow base and a flexible over-ear supporter of the nasal cannula device of FIG. 1.

In detail, each recessed annular section 14a has an outer surface 121 and an inner surface 122. According to the present embodiment, each recessed annular section 14a is recessed from the outer surface 121 of each nasal joint tube 12. Each recessed annular section 14a has a length e equal to or shorter than one half of an inside diameter f of each recessed annular section 14a.

Furthermore, a block ring 123 protrudes outwardly from the outer surface 121 of each nasal joint tube 12, and each recessed annular section 14a is disposed between each junction ring 13 and each block ring 123. Each junction ring 13 is a conical annular block 15 protruding outwardly from the cannula body 1. Each conical annular block 15 has an outer surface 151 and an inner surface 152. The inner surface 152 of each conical annular block 15 includes a rounded surface 153.

Furthermore, the cannula body 1 includes a top surface 16, a left side surface 17 and a right side surface 18. The two nasal joint tubes 12 are extended from the top surface 16. The left side surface 17 includes a first through hole 171 communicating with the accommodating chamber 11, and the right side surface 18 includes a second through hole 181 communicating with the accommodating chamber 11.

Referring to FIGS. 1 to 7, the nasal cannula device 10 includes a hollow base 2. The hollow base 2 is inserted through the first through hole 171 and the second through hole 181 and disposed in the accommodating chamber 11, so that the cannula body 1 receives the hollow base 2. The cannula body 1 consists of rubber or silicon, and the hollow base 2 consists of plastic; however, the present invention is not limited in this regard.

Moreover, the hollow base 2 includes a top end 21, a left end 22 exposed from the first through hole 171, a right end 23 exposed from the second through hole 181, and a gas chamber 24. An opening 211 communicating with the gas chamber 24 is disposed on the top end 21. The opening 211 is disposed corresponding to the two nasal joint tubes 12. One of the left end 22 and the right end 23 is a closed end 25 closing the gas chamber 24, and the other one of the left end 22 and the right end 23 is a connection tube 26 communicating with the gas chamber 24. The gas delivery tube 100 is coupled to the connection tube 26 and communicates with the connection tube 26.

Furthermore, the cannula body 1 includes an annular recess 19 inside. An annular wall 212 is extended from the top end 21, an annular flange 213 protrudes outwardly from an end portion of the annular wall 212, the annular flange 213 is engaged with the annular recess 19 to make the cannula body 1 and the hollow base 2 assembled firmly and stably, and the opening 211 is formed within the annular flange 213.

Figure 6:
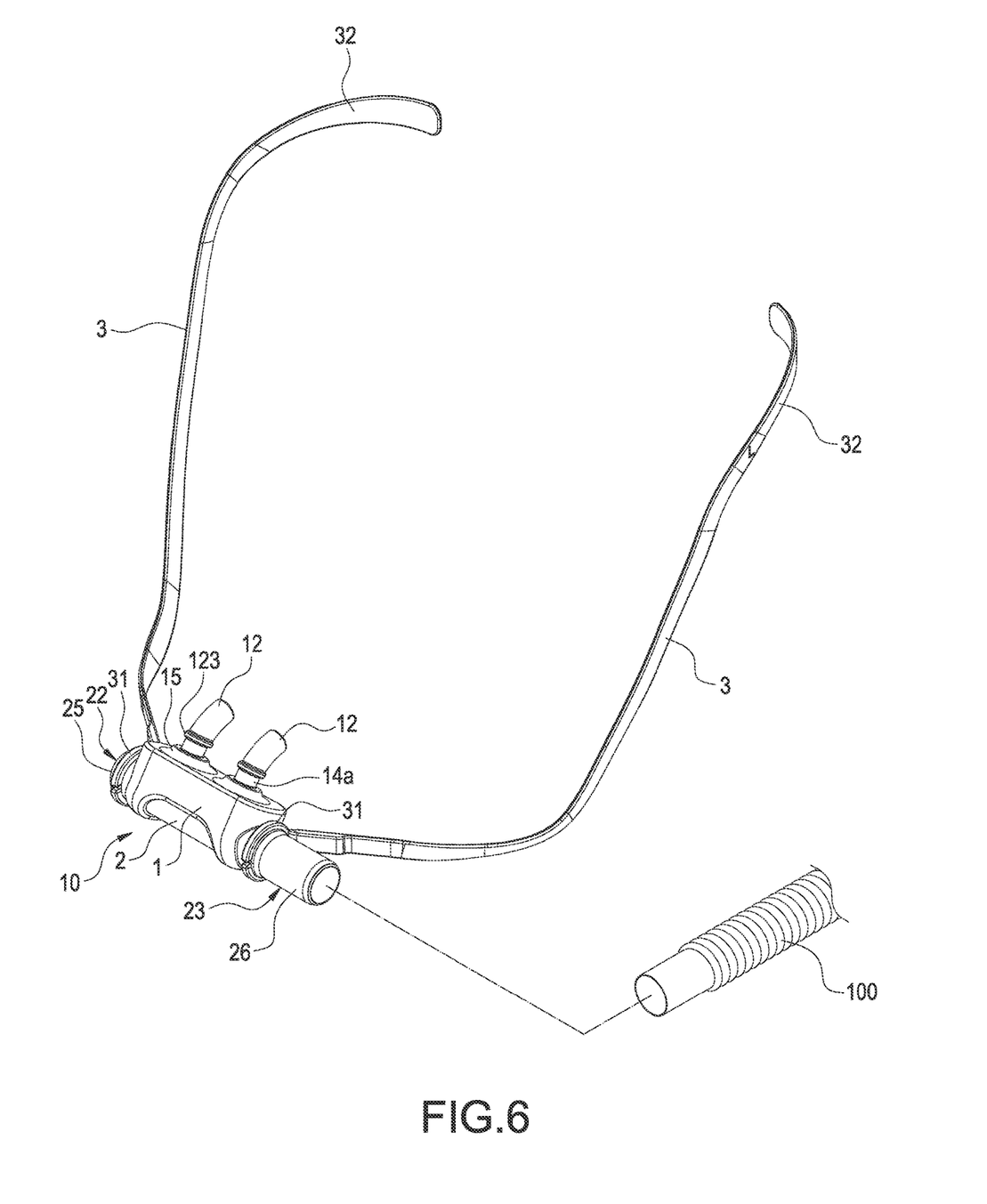
FIG. 6 is a perspective assembled view illustrating the hollow base and the flexible over-ear supporter of the nasal cannula device of FIG. 1.
Figure 7:
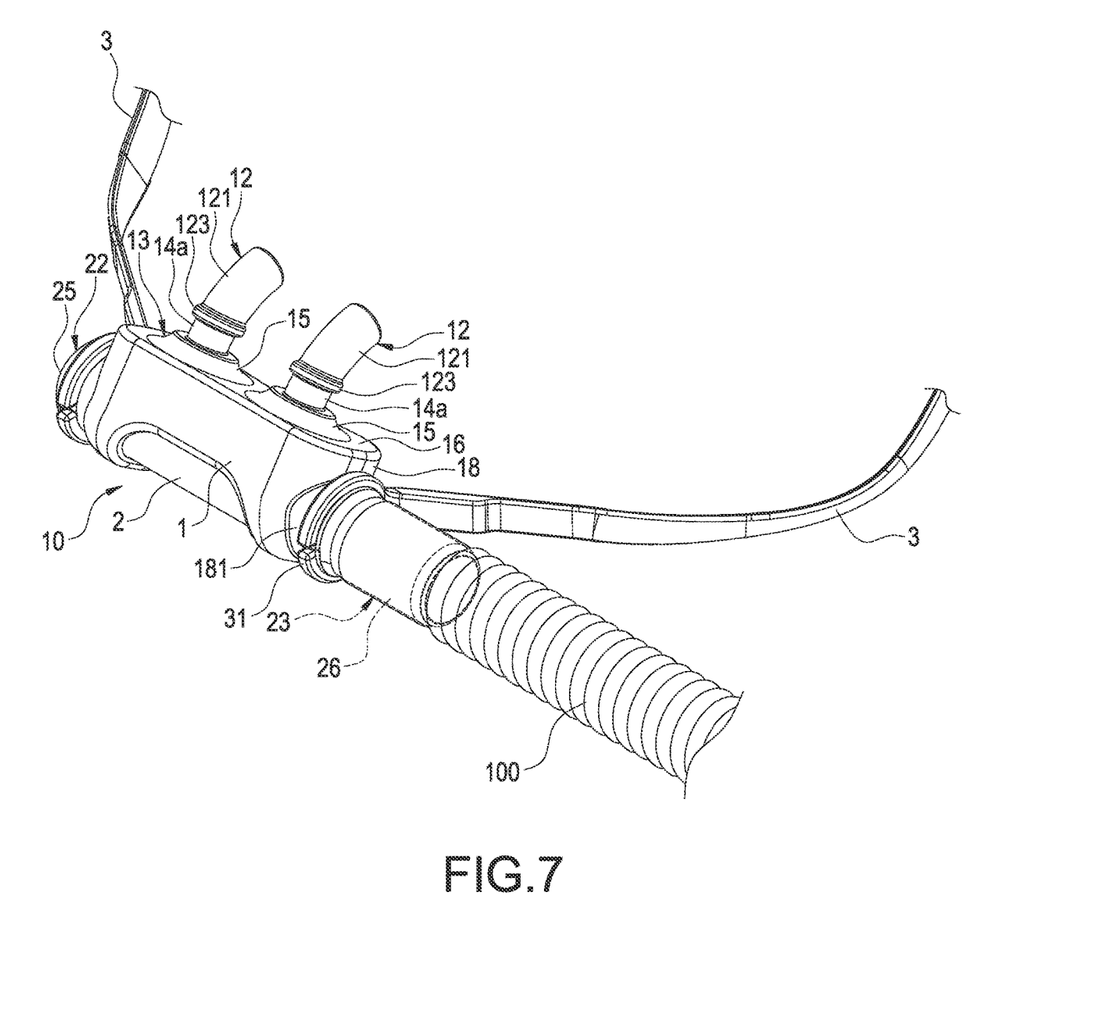
FIG. 7 is a perspective assembled view illustrating the hollow base and a gas delivery tube of the nasal cannula device of FIG. 1.

As shown in FIGS. 6 and 7, in the present embodiment, the connection tube 26 is formed at the right end 23 of the hollow base 2, and the gas delivery tube 100 is disposed at the right side of a patient. Alternatively, the hollow base 2 can be turned 180 degrees and then received in the cannula body 1, so that the connection tube 26 is disposed at the left end 22 of the hollow base 2, and the gas delivery tube 100 is disposed at the left side of the patient. By turning the hollow base 2 180 degrees, the connection tube 26 can be disposed at the left end 22 or the right end 23 of the hollow base 2.

Referring to FIG. 1 and FIGS. 5 to 7, the nasal cannula device 10 further includes two flexible over-ear supporters 3, a C-shaped fastener 31 is extended from one end of each flexible over-ear supporter 3, and an over-ear leg 32 is extended from the other end of each flexible over-ear supporter 3. One of the C-shaped fasteners 31 is fastened to the left end 22, the other C-shaped fastener 31 is fastened to the right end 23. One end of the flexible over-ear supporter 3 is assembled to or detached from the hollow base 2 by means of the C-shaped fastener 31, and the other end of the flexible over-ear fastener 3 is rested on one ear of the patient. The flexible over-ear supporter 3 is slightly deformable to fit the patient's head and increase wearing comfort.

Please refer to FIG. 4 and FIGS. 5 to 7 for the nasal cannula device 10 in use. The two nasal joint tubes 12 are inserted in two nostrils of the patient. A therapeutic gas is delivered into the nostrils of the patient through in sequence the gas delivery tube 100, the connection tube 26, the gas chamber 24, the opening 211, the nasal joint tubes 12 for respiratory therapy.

Moreover, each nasal joint tube 12 includes a recessed annular section 14a recessed at one side of each junction ring 13, the recessed annular section 14a having a thickness d smaller than a thickness a of the cannula body 1, a thickness b of each nasal joint tube 12 and a thickness c of each junction ring 13. Therefore, when the nasal joint tube 12 is under stress, the stress is mainly directed to the recessed annular section 14a since it has the thinnest thickness d, so other portions of the nasal joint tube 12 is prevented from deformation, and only the recessed annular section 14a deforms. Connected to the junction ring 13, a portion of the recessed annular section close to the junction ring 13 thus has sufficient strength to resist deformation and is prevented from being overly bent to cause closing of the nasal joint tube 12. Therefore, the recessed annular section 14a does not overly bend to close the nasal joint tube 12, and therefore the nasal cannula device 10 can deliver the therapeutic gas smoothly.

Each recessed annular section 14a has a length e equal to or shorter than one half of an inside diameter f of each recessed annular section 14a. Because the length e is short, when the recessed annular section 14a bends inwardly, a tube opening of the recessed annular section 14a is not closed by bending of the recessed annular section 14a. In other words, the nasal joint tube 12 is not closed by bending of the recessed annular section 14a, and as a result, the nasal cannula device 10 can deliver the therapeutic gas smoothly.

Furthermore, the block ring 123 protrudes outwardly from the outer surface 121 of each nasal joint tube 12, each junction ring 13 is the conical annular block 15 protruding outwardly from the cannula body 1, and the inner surface 152 of each conical annular block 15 includes the rounded surface 153. Accordingly, when the nasal joint tube 12 is inserted into the nostril of the patient, the block ring 123 and the conical annular block 15 are in contact with an inner surface of the nostril, and thereby the inner surface of the nostril does not make large-area contact with the cannula body 1 and the nasal joint tube 12. This configuration improves wearing comfort of the nasal cannula device 10. In addition, the rounded surface 153 having a curved smooth surface prevents airflow interference or noises from occurring when the therapeutic gas passed by the rounded surface 153.

Figure 8:
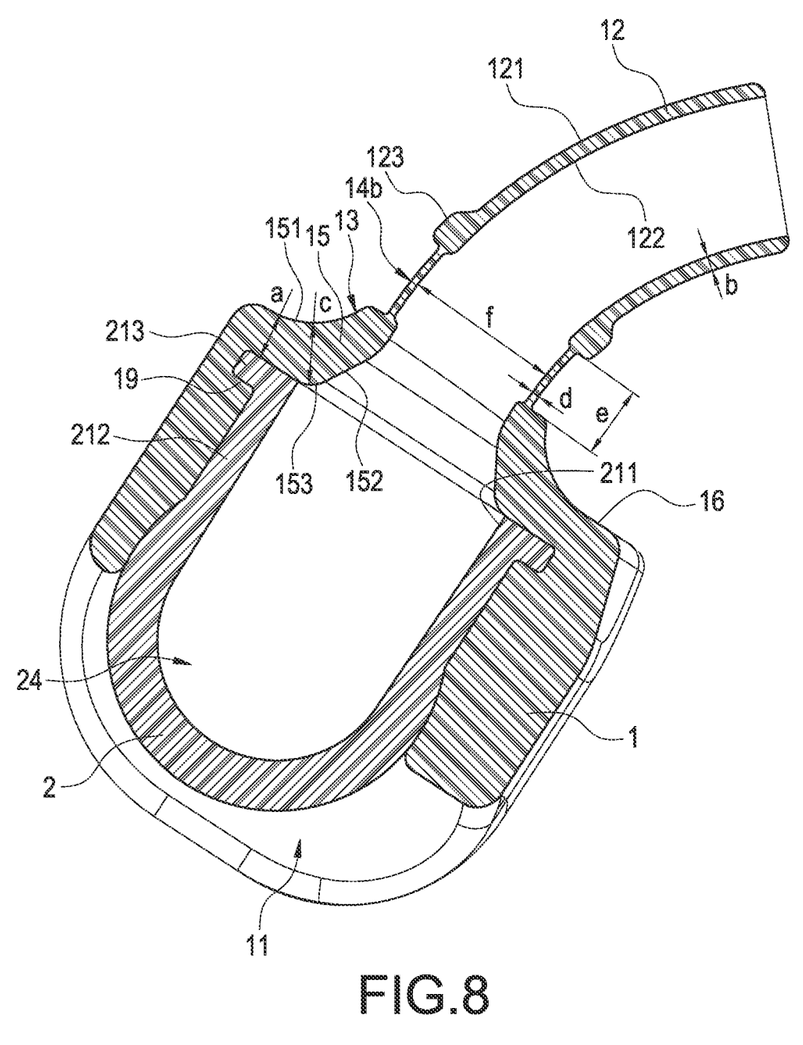
FIG. 8 is a partial cross-sectional view illustrating the nasal cannula device according to the second embodiment of the present invention.

Please refer to FIG. 8 illustrating the nasal cannula device 10 according to the second embodiment of the present invention. The second embodiment is similar to the first embodiment with the difference that each recessed annular section 14b of the second embodiment is recessed from the inner surface 122 of each nasal joint tube 12. The recessed annular section 14b having the thickness d smaller than the thickness a of the cannula body 1, the thickness b of each nasal joint tube 12 and the thickness c of each junction ring 13. When the nasal joint tube 12 is under stress, the stress is mainly directed to the recessed annular section 14b since it has the thinnest thickness d, and therefore the second embodiment achieves the same effects and provides the same functions as the first embodiment.

Figure 9:
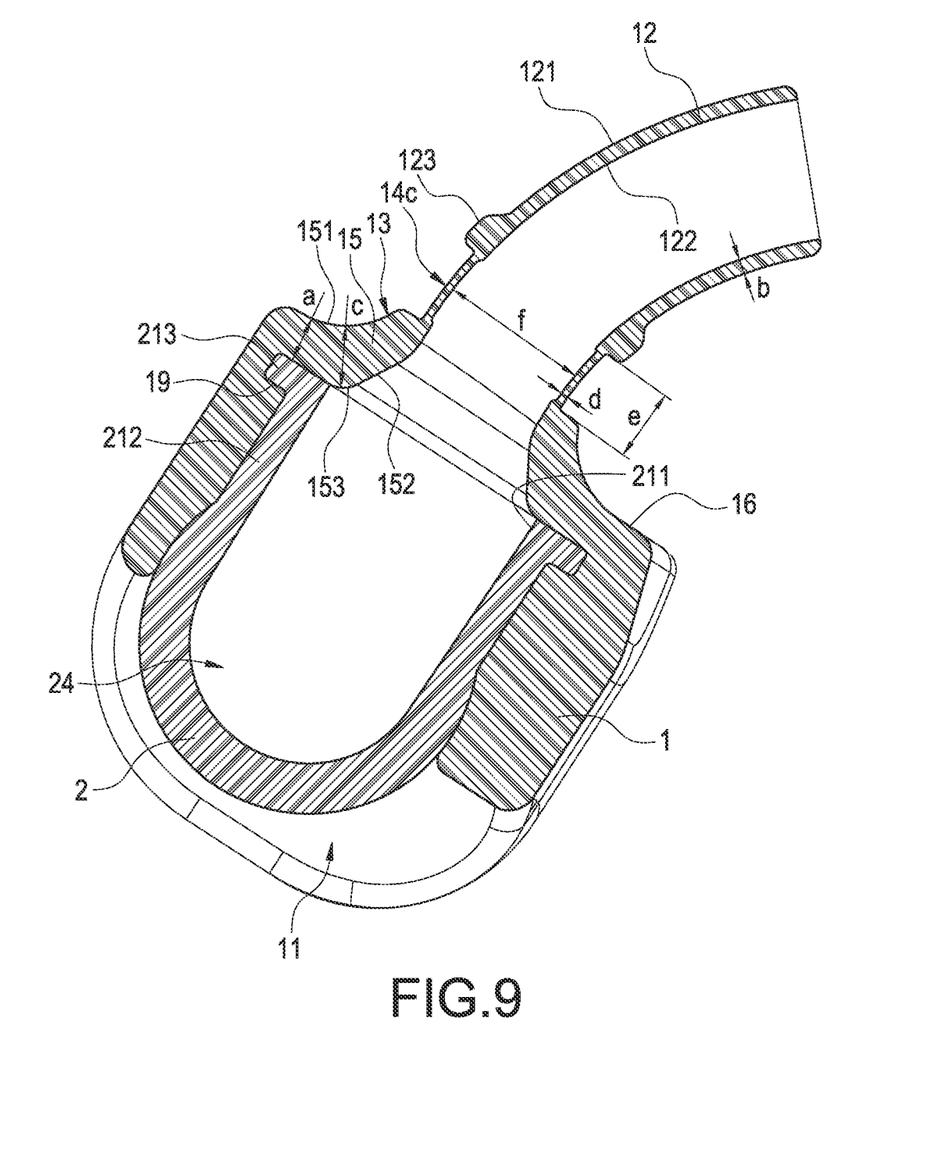
FIG. 9 is a partial cross-sectional view illustrating the nasal cannula device according to the third embodiment of the present invention.

Please refer to FIG. 9 illustrating the nasal cannula device 10 according to the third embodiment of the present invention. The third embodiment is similar to the first embodiment with the difference that each recessed annular section 14c of the third embodiment is recessed from both the inner surface 122 and the outer surface 121 of each nasal joint tube 12. The recessed annular section 14c having the thickness d smaller than the thickness a of the cannula body 1, the thickness b of each nasal joint tube 12 and the thickness c of each junction ring 13.

When the nasal joint tube 12 is under stress, the stress is mainly directed to the recessed annular section 14c since it has the thinnest thickness d, and therefore the third embodiment achieves the same effects and provides the same functions as the first embodiment.

Figure 10:
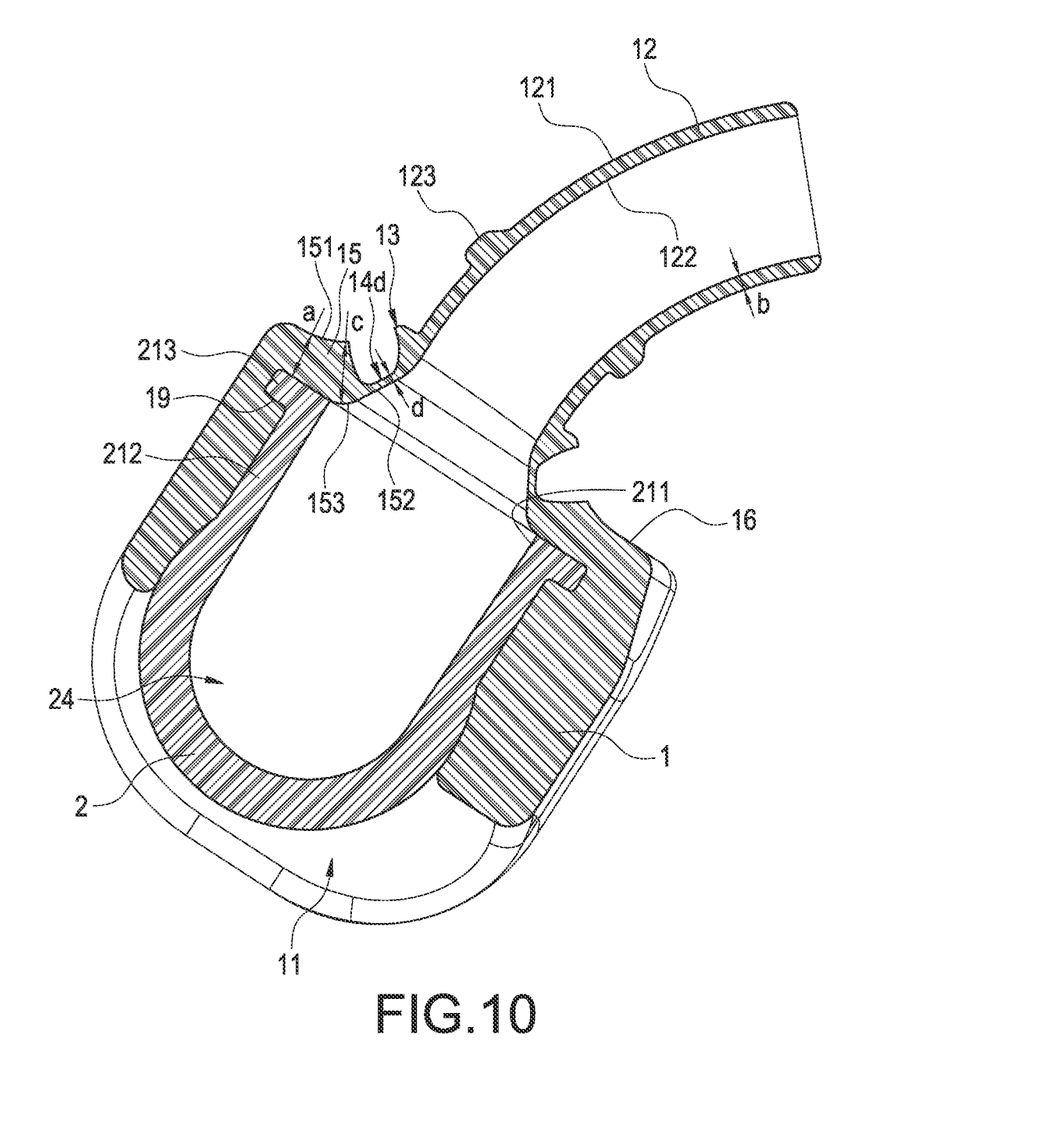
FIG. 10 is a partial cross-sectional view illustrating the nasal cannula device according to the fourth embodiment of the present invention.

Please refer to FIG. 10 illustrating the nasal cannula device 10 according to the fourth embodiment of the present invention. The fourth embodiment is similar to the first embodiment with the difference that each recessed annular section 14d of the fourth embodiment is recessed from the outer surface 151 of each conical annular block 15.

In detail, each recessed annular section 14d is recessed from the outer surface 151 of each conical annular block 15. The recessed annular section 14d having the thickness d smaller than the thickness a of the cannula body 1, the thickness b of each nasal joint tube 12 and the thickness c of each junction ring 13. When the nasal joint tube 12 is under stress, the stress is mainly directed to the recessed annular section 14d since it has the thinnest thickness d, and therefore the fourth embodiment achieves the same effects and provides the same functions as the first embodiment.

Moreover, the recessed annular section 14d is formed on the cannula body 1. Therefore, deformation of the recessed annular section 14d does not affect a tube opening of the nasal cannula tube 12. As a result, there is no limitation on the length of the recessed annular section 14d.

As can be appreciated from FIGS. 4, 8 and 9, each recessed annular section 14d is recessed from the outer surface 151 of each conical annular block 15. Alternatively, each recessed annular section 14d can be recessed from the inner surface 152 of each conical annular block 15, or each recessed annular section 14d can also be recessed from both the outer surface 151 and the inner surface 152 of each conical annular block 15.

Figure 11:
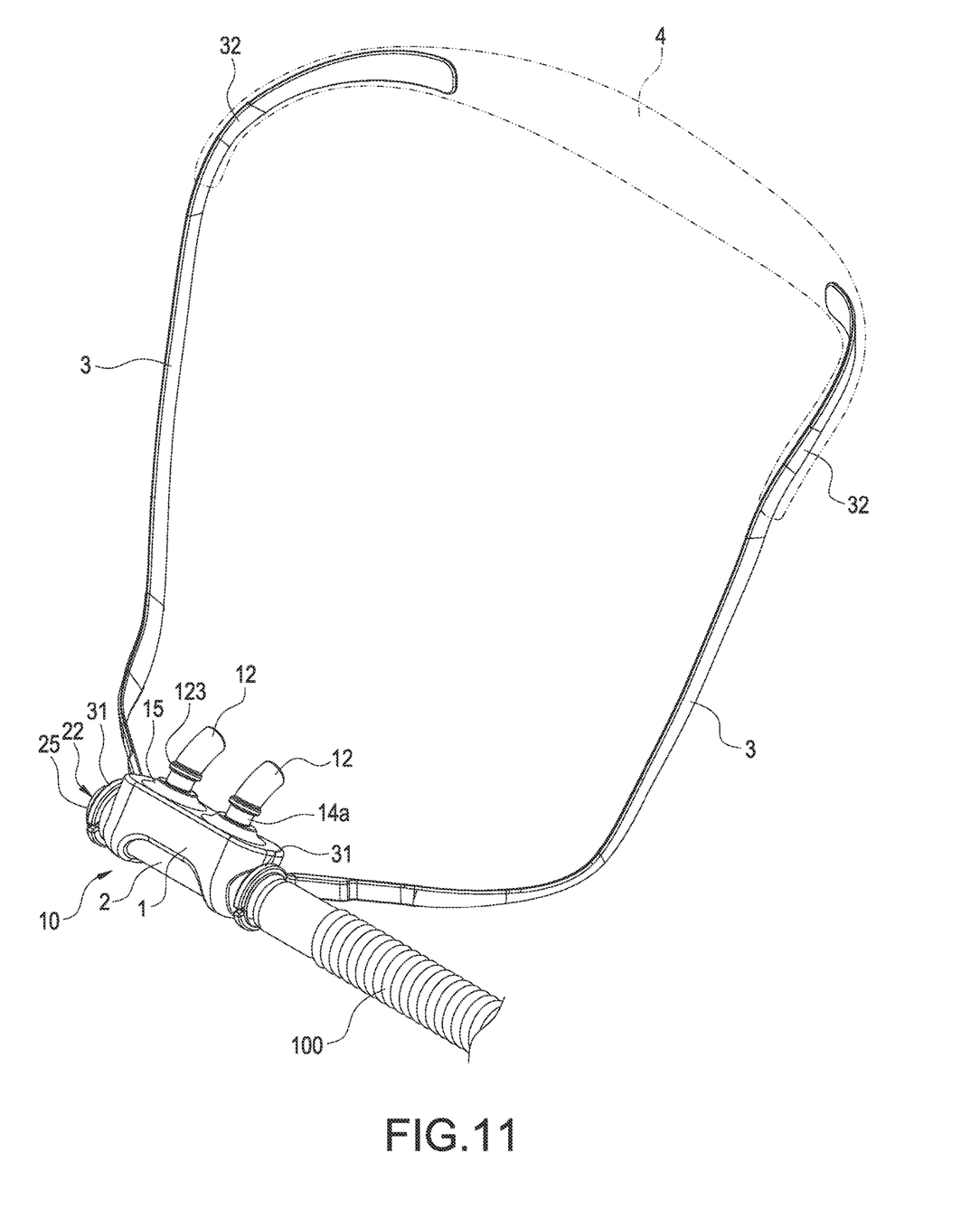
FIG. 11 is a perspective assembled view illustrating the nasal cannula device according to the fifth embodiment of the present invention.

Please refer to FIG. 11 showing the nasal cannula device 10 according to the fifth embodiment of the present invention. The fifth embodiment is similar to the first embodiment with the difference that the nasal cannula device 10 further includes an elastic fabric cover 4. Two ends of the elastic fabric cover 4 receive the two over-ear legs 32, respectively, so that the flexible over-ear supporter 3 and the elastic fabric cover 4 can surround and closely fit the patient's head, and thus the nasal joint tube 12 is more stably inserted in the patient's nasal cavity and prevented from being offset or detached from the nasal cavity.

In summary, the nasal cannula device 10 of the present invention can achieve anticipated objectives and solve the conventional defects. The present invention also has industrial applicability, novelty and non-obviousness, so the present invention completely complies with the requirements of patentability. Therefore, a request to patent the present invention is filed pursuant to patent law. Examination is kindly requested, and allowance of the present application is solicited to protect the rights of the inventor.

What is claimed is:
1. A nasal cannula device comprising:
   a cannula body including:
      a body portion; and
      a nasal joint tube, which includes
         a tube section;
         a block ring protruding outwardly from an outer surface of the tube section; and
         a recessed annular section disposed between the body portion and the block ring,
   wherein:
      the recessed annular section has a thickness smaller than that of the tube section, a substantially uniform diameter, and a length equal to or shorter than one half of an inside diameter of the recessed annular section.

* * * * *